(12) United States Patent
McKay

(10) Patent No.: US 9,132,194 B2
(45) Date of Patent: Sep. 15, 2015

(54) MEDICAL DEVICES AND METHODS COMPRISING AN ADHESIVE SHEET CONTAINING A DRUG DEPOT

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 273 days.

(21) Appl. No.: 13/180,685

(22) Filed: Jul. 12, 2011

(65) Prior Publication Data

US 2013/0018321 A1    Jan. 17, 2013

(51) Int. Cl.
*A61K 47/34* (2006.01)
*A61K 9/00* (2006.01)

(52) U.S. Cl.
CPC ............... *A61K 47/34* (2013.01); *A61K 9/0024* (2013.01)

(58) Field of Classification Search
None
See application file for complete search history.

(56) References Cited

U.S. PATENT DOCUMENTS

| | | | |
|---|---|---|---|
| 5,759,583 | A | 6/1998 | Iwamoto et al. |
| 5,849,493 | A | 12/1998 | Montminey et al. |
| 5,942,241 | A | 8/1999 | Chasin et al. |
| 6,069,129 | A | 5/2000 | Sandberg et al. |
| 6,179,862 | B1 | 1/2001 | Sawhney |
| 6,248,345 | B1 | 6/2001 | Goldenheim et al. |
| 6,287,588 | B1 | 9/2001 | Shih et al. |
| 6,326,020 | B1 | 12/2001 | Kohane et al. |
| 6,326,025 | B1 | 12/2001 | Sigler et al. |
| 6,331,311 | B1 | 12/2001 | Brodbeck et al. |
| 6,428,804 | B1 | 8/2002 | Suzuki et al. |
| 6,461,631 | B1 | 10/2002 | Dunn et al. |
| 6,524,607 | B1 | 2/2003 | Goldenheim et al. |
| 6,534,081 | B2 | 3/2003 | Goldenheim et al. |
| 6,589,549 | B2 | 7/2003 | Shih et al. |
| 6,630,155 | B1 | 10/2003 | Chandrashekar et al. |
| 6,632,457 | B1 | 10/2003 | Sawhney |
| 6,773,714 | B2 | 8/2004 | Dunn et al. |
| 6,921,541 | B2 | 7/2005 | Chasin et al. |
| 7,287,983 | B2 | 10/2007 | Ilan |
| 7,727,954 | B2 | 6/2010 | McKay |

(Continued)

FOREIGN PATENT DOCUMENTS

| CN | 1117877 C | 8/2003 |
|---|---|---|
| CN | 1660068 A | 8/2005 |

(Continued)

OTHER PUBLICATIONS

Atrigel, Drug Delivery Platform, QLT USA, Inc., Revised Jul. 2006, 2 pages.

*Primary Examiner* — Jeffrey T Palenik
(74) *Attorney, Agent, or Firm* — Sorell Lenna & Schmidt LLP

(57) ABSTRACT

Improved medical devices and methods are provided that are implantable at or near a target tissue site beneath the skin of a patient, the medical device comprises an adhesive sheet having a region configured to receive a drug depot, the drug depot disposed within the region of the adhesive sheet and the drug depot having at least one surface configured to release a therapeutically effective amount of the drug over a period of at least one day, wherein the adhesive sheet limits movement of the medical device at or near the target tissue site. In some embodiments, the medical device provided can include an effective amount of at least one analgesic and/or at least one anti-inflammatory agent at or near a target site, and can reduce, prevent or treat inflammation and/or pain, particularly postoperative pain or orthopedic degenerative pathology pain.

19 Claims, 3 Drawing Sheets

(56) References Cited

U.S. PATENT DOCUMENTS

| | | |
|---|---|---|
| 2002/0009454 A1 | 1/2002 | Boone et al. |
| 2002/0090398 A1 | 7/2002 | Dunn et al. |
| 2004/0072799 A1 | 4/2004 | Li et al. |
| 2004/0082540 A1 | 4/2004 | Hermida Ochoa |
| 2004/0109893 A1 | 6/2004 | Chen et al. |
| 2004/0214793 A1 | 10/2004 | Hermida Ochoa |
| 2004/0219214 A1 | 11/2004 | Gravett et al. |
| 2005/0142163 A1 | 6/2005 | Hunter et al. |
| 2005/0153090 A1* | 7/2005 | Marchitto et al. ........... 428/40.1 |
| 2005/0175709 A1 | 8/2005 | Baty, III et al. |
| 2005/0186261 A1 | 8/2005 | Avelar et al. |
| 2005/0197293 A1 | 9/2005 | Mellis et al. |
| 2005/0288620 A1 | 12/2005 | Shippert |
| 2006/0074422 A1 | 4/2006 | Story et al. |
| 2006/0104966 A1 | 5/2006 | Green et al. |
| 2006/0105026 A1 | 5/2006 | Fortune et al. |
| 2006/0148903 A1 | 7/2006 | Burch et al. |
| 2006/0153815 A1 | 7/2006 | Seyda et al. |
| 2006/0189944 A1 | 8/2006 | Campbell et al. |
| 2006/0228391 A1 | 10/2006 | Seyedin et al. |
| 2006/0253094 A1 | 11/2006 | Hadba et al. |
| 2007/0021358 A1 | 1/2007 | Edelman et al. |
| 2007/0066864 A1 | 3/2007 | Forde |
| 2007/0104769 A1 | 5/2007 | Feng et al. |
| 2007/0156180 A1 | 7/2007 | Jaax et al. |
| 2007/0202074 A1 | 8/2007 | Shalaby |
| 2007/0224235 A1 | 9/2007 | Tenney et al. |
| 2007/0243225 A1 | 10/2007 | McKay |
| 2007/0243228 A1 | 10/2007 | McKay |
| 2007/0253994 A1 | 11/2007 | Hildebrand |
| 2007/0286891 A1 | 12/2007 | Kettlewell et al. |
| 2007/0299155 A1 | 12/2007 | Carpenter et al. |
| 2008/0009830 A1 | 1/2008 | Fujimoto et al. |
| 2008/0038351 A1 | 2/2008 | Beals et al. |
| 2008/0039547 A1 | 2/2008 | Khatri et al. |
| 2008/0039548 A1 | 2/2008 | Zavatsky et al. |
| 2008/0091207 A1 | 4/2008 | Truckai et al. |
| 2008/0096975 A1 | 4/2008 | Guan et al. |
| 2009/0018575 A1 | 1/2009 | Fortune et al. |
| 2009/0030451 A1 | 1/2009 | Hadba et al. |
| 2009/0044895 A1 | 2/2009 | Fortune et al. |
| 2009/0264491 A1* | 10/2009 | McKay et al. ................ 514/401 |
| 2009/0287129 A1 | 11/2009 | Boehringer et al. |
| 2010/0003329 A1 | 1/2010 | Elisseeff |
| 2010/0080838 A1 | 4/2010 | Stopek |
| 2010/0173843 A1 | 7/2010 | Hnojewyj |
| 2010/0215659 A1 | 8/2010 | Ladet |
| 2011/0105641 A1 | 5/2011 | Khatri et al. |
| 2011/0111034 A1 | 5/2011 | Wang et al. |
| 2012/0179176 A1* | 7/2012 | Wilson et al. ................ 606/151 |

FOREIGN PATENT DOCUMENTS

| | | |
|---|---|---|
| EP | 0256893 B1 | 2/1988 |
| EP | 0651985 B1 | 5/1995 |
| EP | 1124594 B1 | 8/2001 |
| GB | 2023006 A | 12/1979 |
| GB | 2276087 B | 9/1994 |
| JP | 200675208 A | 3/2006 |
| WO | 03005961 A2 | 1/2003 |
| WO | 2009019516 A2 | 2/2009 |

* cited by examiner

MEDICAL DEVICES AND METHODS COMPRISING AN ADHESIVE SHEET CONTAINING A DRUG DEPOT

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, medical devices comprising drug depots have been developed which allow a drug to be introduced or administered to sites beneath the skin of a patient so that the drug is slowly released over a long period of time. Such medical devices allow the drug to be released from the device in a relatively uniform dose over days, weeks, or months. This method of administering drugs is becoming especially important for contraceptives and cancer drugs that are implanted subcutaneously.

Sometimes, after the medical device is implanted at the treatment site, the medical device may migrate from the implant site prior to surgical closure (e.g., floats off in blood or shifts as tissues are repositioned during surgical site closure) or as physiological conditions change (e.g., repair and regeneration of cells, tissue ingrowth, movement at implant site, etc.). At times, this may reduce efficacy of the drug as the medical device migrates away from the implant site and lodges in a distant site. If this occurs, the medical device will have to be removed from the distant site and have to be reinserted causing additional physical and psychological trauma to a patient. In some cases, if the medical device migrates into a joint, the medical device may inhibit movement. In more severe cases, if the medical device migrates, it may restrict blood flow causing an ischemic event (e.g., embolism, necrosis, infarction, etc.), which could be detrimental to the patient.

Postoperative pain tends to be a difficult condition to treat and may be detrimental to the patient if not properly treated. The site of the surgery has a profound effect upon the degree of postoperative pain a patient may suffer. In general, operations on the thorax and upper abdomen are more painful than operations on the lower abdomen, which in turn are more painful than peripheral operations on the limbs. However, any operation involving a body cavity, large joint surfaces, the spine or deep tissues should be regarded as painful. In particular, operations on the thorax or upper abdomen may produce widespread changes in pulmonary function, an increase in abdominal muscle tone and an associated decrease in diaphragmatic function. The result will be an inability to cough and clear secretions, which may lead to lung collapse and pneumonia. Prolonged pain can reduce physical activity and lead to venous stasis and an increased risk of deep vein thrombosis and consequently pulmonary embolism. In addition, there can be widespread effects on gut and urinary tract motility, which may lead in turn to postoperative ileus, nausea, vomiting and urinary retention. These problems are unpleasant for the patient and may prolong hospital stay and are exacerbated if after implantation the drug depot migrates away from the implant site.

There are many painful diseases or conditions, besides post-operative pain, that are chronic in nature and require proper pain and/or inflammation control. Such diseases or conditions include rheumatoid arthritis, osteoarthritis, sciatica, carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, orthopedic pain due to inflammation, TMJ, tendons, ligaments, muscles, orthopedic degenerative pathology pain, or the like.

One particularly painful disease is sciatica. Sciatica is a chronic disease that often can be very debilitating and may take a terrible toll on those with the disease as well as their families, friends and caregivers. Sciatica is a very painful disease associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area.

New medical devices and methods are needed, which can easily allow accurate and precise placement of the device. When implanting several medical devices at a time, medical device compositions and methods are needed that accurately and precisely allow placement of the device in a manner that optimizes location, accurate spacing, and drug distribution. New medical devices and methods are also needed to effectively treat post-operative pain and/or inflammation or chronic pain and/or inflammation.

SUMMARY

A new implantable medical device that improves drug efficacy and reduces unwanted migration of the medical device is provided. In various embodiments, new medical devices and methods are provided that effectively prevent, treat or reduce postoperative pain and/or inflammation by providing consistent analgesic and/or anti-inflammatory efficacy at the target tissue site of pain generation. In various embodiments, new medical devices and methods are provided that effectively prevent, treat or reduce chronic pain and/or inflammation by providing consistent analgesic and/or anti-inflammatory efficacy at the target tissue site of pain generation.

In various embodiments, an adhesive sheet is provided that has a drug depot disposed within one of its regions allowing the surgeon to easily apply pressure to the adhesive sheet causing the drug depot to adhere to the desired target tissue site. In this way, migration of the drug depot away from the target tissue site is inhibited and/or prevented. In various embodiments, the medical device has a removable covering so that the user can "peel and press" the medical device directly at the target tissue site.

In one embodiment, there is a medical device implantable at or near a target tissue site beneath the skin of a patient, the medical device comprising an adhesive sheet having a region configured to receive a drug depot, the drug depot disposed within the region of the adhesive sheet and the drug depot having at least one surface configured to release a therapeutically effective amount of the drug over a period of at least one day, wherein the adhesive sheet limits movement of the medical device at or near the target tissue site.

In another embodiment, there is a medical device implantable at or near a target tissue site beneath the skin of a patient, the medical device comprising an adhesive sheet having a region configured to receive a drug depot, the drug depot disposed within the region of the adhesive sheet and the drug depot having a therapeutically effective amount of a drug and at least one surface adapted to release the therapeutically effective amount of the drug, wherein the adhesive sheet limits movement of the medical device at or near the target tissue site and the at least one surface of the drug depot releases about 5% to about 45% of an analgesic relative to a total amount of the analgesic loaded in the medical device over a first period of up to 48 hours and about 55% to about 95% of the analgesic relative to a total amount of the analgesic loaded in the medical device over a subsequent period of at least one day.

In yet another embodiment, there is a method of treating postoperative pain or inflammation in a patient in need of such treatment, the method comprising positioning a medical device at or near a target tissue site beneath the skin of a patient, the medical device comprising an adhesive sheet having an adhesive material disposed on all or a portion of the adhesive sheet, the adhesive sheet having a region containing a drug depot disposed within the region, and the drug depot having a therapeutically effective amount of a drug and at least one surface adapted to release the therapeutically effective amount of the drug over a period of at least one day, and applying pressure to the adhesive sheet and allowing the adhesive material to adhere to the target tissue site so as to limit movement of the medical device at or near the target tissue site. In some embodiments, the medical device is a biodegradable polymer adhesive and drug depot.

The medical device may: (i) consist of only the analgesic and/or anti-inflammatory agent (or one or more of its pharmaceutically acceptable salts, esterified forms or non-esterified forms thereof), the adhesive and the biodegradable polymer(s); or (ii) consist essentially of the analgesic and/or anti-inflammatory agent (or one or more of its pharmaceutically acceptable salts, esterified forms or non-esterified forms thereof), the adhesive and the biodegradable polymer(s), or (iii) comprise the analgesic and/or anti-inflammatory agent (or one or more of its pharmaceutically acceptable salts, esterified forms or non-esterified forms thereof), the adhesive and the biodegradable polymer(s); or (iv) consist essentially of the analgesic and/or anti-inflammatory agent (or one or more of its pharmaceutically acceptable salts, esterified forms or non-esterified forms thereof), the adhesive and the biodegradable polymer(s) and one or more other active ingredients, surfactants, excipients or other ingredients or combinations thereof. When there are other active ingredients, surfactants, pore forming agents, plasticizers, lubricants, excipients or other ingredients or combinations thereof in the formulation, in some embodiments these other compounds or combinations thereof comprise less than 50 wt. %. less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWING

In part, other aspects, features, benefits and advantages of the embodiments will be apparent with regard to the following description, appended claims and accompanying drawing where:

Figure 1:
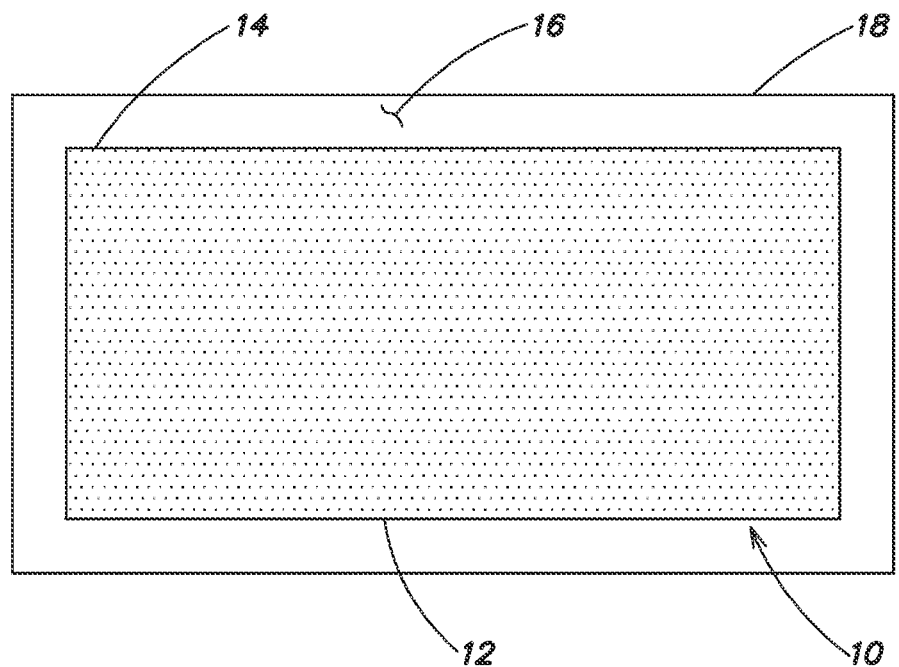
FIG. 1 illustrates a front view of one embodiment of the implantable medical device having an adhesive sheet that has a region containing a drug depot in the form of a strip that releases the therapeutic agent. The adhesive material is disposed on the back of the sheet.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a medical device" includes one, two, three or more medical devices.

The term "implantable" as utilized herein refers to a biocompatible medical device (e.g., drug depot) retaining potential for successful placement within a mammal. The expression "implantable medical device" and expressions of the like import as utilized herein refers to an object implantable through surgery, injection, or other suitable means whose primary function is achieved either through its physical presence or mechanical properties.

A "drug depot" is the composition in which the therapeutic agent is administered to the target tissue site. Thus, a drug depot may comprise a physical structure to facilitate implantation and retention in a desired site (e.g., ulcer, surgical wound, traumatic wound, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient", "API", or "biological agent." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the medical device provides an optimal drug concentration gradient of the therapeutic agent at a distance of up to about 0.01 cm to about 20 cm from the administration site. A "depot" includes but is not limited to capsules, coatings, matrices, wafers, sheets, strips, ribbons, pills, pellets, microspheres, nanospheres, or other pharmaceutical delivery or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. Typically, the depot will be a solid or semi-solid formulation comprised of a biocompatible material that can be biodegradable.

A "therapeutically effective amount" or "effective amount" is such that when administered, the drug results in alteration of the biological activity, such as, for example, inhibition of inflammation, inhibition of pain, and/or improvement in the healing wound, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments, all or parts (e.g., surfaces, regions, layers, etc.) of the medical device (e.g., drug depot) may be designed for immediate release. In other embodiments the medical device (e.g., drug depot) may be designed for sustained release. In other embodiments, the medical device (e.g., drug depot) comprises one or more immediate release surfaces, layers, regions and one or more sustained release surfaces layers or regions.

The term "sheet" includes a three-dimensional article with a thickness that is considerably less than its other dimensions. Such an article may alternatively be described as a patch or a film. In some embodiments, the sheet has an overall thickness of from 0.01 to 1 mm. In some embodiments, the sheet has an overall thickness of from 0.015 to 0.05 mm. In some embodiments, this does not include the thickness of the drug depot. In some embodiments, the sheet can be rolled or flat.

An "adhesive" includes material that chemically binds the adhesive sheet to the target tissue site. Adhesives can be liquid, semi-solid or in a solid state. The adhesive can be a solvent based adhesive, a polymer dispersion adhesive, a contact adhesive, a pressure sensitive adhesive, a reactive adhesive, such as for example a multi-part adhesive, one part adhesive, heat curing adhesive, moisture curing adhesive, or a combination thereof or the like. The adhesive can be natural or synthetic or a combination thereof. In some embodiments, the adhesive can be disposed or coated on all or portions of the front and/or back of the sheet in a thickness of about 0.1 to about 50 microns.

The term "biodegradable" includes that all or parts of the medical device (e.g., drug depot, adhesive agent, etc.) will degrade over time by the action of enzymes, by hydrolytic action and/or by other similar mechanisms in the human body. In various embodiments, "biodegradable" includes that the medical device can break down or degrade within the body to non-toxic components after or while a therapeutic agent has been or is being released. By "bioerodible" it is meant that the medical device will erode or degrade over time due, at least in part, to contact with substances found in the surrounding tissue, fluids or by cellular action. By "bioabsorbable" it is meant that the medical device will be broken down and absorbed within the human body, for example, by a cell or tissue. "Biocompatible" means that the medical device will not cause substantial tissue irritation or necrosis at the target tissue site.

In some embodiments, the medical device (e.g., drug depot, adhesive sheet) has pores that allow release of the drug from the medical device. The medical device will allow fluid in the device to displace the drug. However, in some embodiments, cell infiltration into the device will be prevented by the size of the pores of the device. In this way, in some embodiments, the medical device should not function as a tissue scaffold and allow tissue growth. Rather, the medical device will solely be utilized for drug delivery. In some embodiments, the pores in the medical device will be less than 250 to 500 microns. This pore size will prevent cells from infiltrating the medical device and laying down scaffolding cells. Thus, in this embodiment, drug will elute from the medical device as fluid enters the device, but cells will be prevented from entering. Pores can be made using, for example a pore forming agent including polyhydroxy compounds such as a carbohydrate, a polyhydroxy aldehyde, a polyhydroxy ketone, a glycogen, an aldose, a sugar, a mono- or polysaccharide, an oligosaccharide, a polyhydroxy carboxylic compound, polyhydroxy ester compound, a cyclodextrin, a polyethylene glycol polymer, a glycerol an alginate, a chitosan, a polypropylene glycol polymer, a polyoxyethylene-polyoxypropylene block co-polymer, agar, or hyaluronic acid or polyhydroxy derivative compounds, hydroxypropyl cellulose, tween, sorbitan, sorbitan monolaurate, sorbitan monopalmitate, sorbitan monostearate, sorbitan tristearate, sorbitan monooleate, or a combination thereof. In some embodiments, where there are little or no pores, the drug will elute out from the drug depot by the action of enzymes, by hydrolytic action and/or by other similar mechanisms in the human body.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the medical device (e.g., drug depot), or a matrix or component thereof, or as the result of metabolic transformation or dissolution of the therapeutic agent(s) or conjugates of therapeutic agent(s). In some embodiments the medical device (e.g., drug depot, adhesive sheet) can have one or more sustained release surface(s), region(s) or layer(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. In some embodiments the medical device (e.g., drug depot, adhesive sheet) can have one or more immediate release surface(s), regions(s) or layer(s).

The two types of formulations (sustain release and immediate release) may be used in conjunction. The sustained release and immediate release may be in one or more of the same medical device (e.g., depot, adhesive sheet). In various embodiments, the sustained release and immediate release may be part of separate medical devices. For example a bolus or immediate release formulation of analgesic and/or anti-inflammatory agent may be placed at or near the target site and a sustain release formulation may also be placed at or near the same site. Thus, even after the bolus becomes completely accessible, the sustain release formulation would continue to provide the active ingredient for the intended tissue.

In various embodiments, the medical device can be designed to cause an initial burst dose of therapeutic agent within the first twenty-four, forty-eight hours, or seventy-two hours after implantation. "Initial burst" or "burst effect" or "bolus dose" refers to the release of therapeutic agent from the medical device (e.g., one or more surfaces, regions or layers of the drug depot, adhesive sheet) during the first twenty-four hours, or forty-eight or seventy-two hours after the device comes in contact with an aqueous fluid (e.g., synovial fluid, cerebral spinal fluid, wound fluid, saline, blood etc.). In some embodiments, the medical device releases 5%, 10%, 15%, 20%, 25%, 30%, 35%, 40%, 45%, or 50% of the total weight of the therapeutic agent loaded in the medical device within the first twenty-four, forty-eight hours, or seventy-two hours after implantation when the device comes into contact with bodily fluid. The "burst effect" or "bolus dose" is believed to be due to the increased release of therapeutic agent from the device (e.g., drug depot, adhesive sheet). In alternative embodiments, the medical device (e.g., drug depot, adhesive sheet) is designed to avoid or reduce this initial burst effect (e.g., by applying an outer polymer coating to the depot or imbedding the drug deep within the polymer, using a polymer having a high molecular weight or combinations thereof, or imbedding drug deep within the adhesive, etc.).

"Analgesic" refers to an agent or compound that can reduce, relieve or eliminate pain. Examples of analgesic agents include but are not limited to acetaminophen, a local anesthetic, such as for example, lidocaine, bupivicaine, ropivacaine, clonidine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papavereturn, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

Examples of a useful statin for treatment of pain and/or inflammation include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to a drug (e.g., an anti-inflammatory agent, analgesic, and the like) the inventor(s) are also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

"Treating" or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of the effective dosages of at least one analgesic agent and at least one anti-inflammatory agent may be used to prevent, treat or relieve the symptoms of pain and/or inflammation.

"Localized" delivery includes delivery where one or more drugs are deposited within a tissue, for example, a nerve root of the nervous system or a region of the brain, or in close proximity (within about 10 cm, or preferably within about 5 cm, for example) thereto. A "targeted delivery system" provides delivery of one or more drugs depots having a quantity of therapeutic agent that can be deposited at or near the target site as needed for treatment of pain, inflammation or other disease or condition.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

"Localized" delivery includes delivery where one or more medical devices are deposited within a tissue, for example, epidermis, dermis, lower dermis, muscle, oil and sweat glands, tendons, ligaments, etc. or in close proximity (within about 0.1 cm, or preferably within about 5 cm, for example) thereto. For example, the medical device containing a drug can deliver a dose of it locally that is 20%, 30%, 40%, 50%, 60%, 70%, 80%, 90%, 95%, 99%, 99.9% or 99.999% less than the oral dosage or IV or IM systemic dose. In turn, systemic side effects, such as for example, liver transaminase elevations, hepatitis, liver failure, myopathy, constipation, etc. may be reduced or eliminated. In some embodiments, the medical device is not delivered to the eye and does not include eye formulations.

The phrase "pain management medication" includes one or more therapeutic agents that are administered in addition to the therapeutic steroid to prevent, alleviate or remove pain entirely. These include anti-inflammatory agents, muscle relaxants, analgesics, anesthetics, narcotics, and so forth, or combinations thereof.

The phrase "release rate profile" refers to the percentage of active ingredient that is released over fixed units of time, e.g., mcg/hr, mcg/day, mg/day, 10% per day for ten days, etc. As persons of ordinary skill know, a release rate profile may, but need not, be linear. By way of a non-limiting example, the medical device (e.g., drug depot) may be a ribbon-like fiber that releases the therapeutic agent at or near the wound over a period of time.

The term "solid" is intended to mean a rigid material, while, "semi-solid" is intended to mean a material that has some degree of flexibility, thereby allowing the depot to bend and conform to the surrounding tissue requirements. In some embodiments, the medical device has a sufficient flexibility to allow placement within the target tissue site. In some embodiments, the medical device is provided that hardens or stiffens after delivery. Typically, hardening formulations may have a pre-dosed modulus of elasticity in the range of about $1 \times^- 10^2$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening formulations (after delivery), in some embodiments, may have a rubbery consistency and have a modulus of elasticity in the range of about $1 \times^- 10^2$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$ "Targeted delivery system" provides delivery of one or more medical devices (e.g., drugs depots) having a quantity of therapeutic agent that can be deposited at or near the target site as needed for treatment of the condition or disease.

In some embodiments, the medical device may comprise DLG. The abbreviation "DLG" refers to poly(DL-lactide-co-glycolide). In some embodiments, the medical device may comprise DL. The abbreviation "DL" refers to poly(DL-lactide). In some embodiments, the medical device may comprise LG. The abbreviation "LG" refers to poly(L-lactide-co-glycolide). In some embodiments, the medical device may comprise CL. The abbreviation "CL" refers to polycaprolactone. In some embodiments, the medical device may comprise DLCL. The abbreviation "DLCL" refers to poly(DL-lactide-co-caprolactone). In some embodiments, the medical device may comprise LCL. The abbreviation "LCL" refers to poly(L-lactide-co-caprolactone). In some embodiments, the medical device may comprise G. The abbreviation "G" refers to polyglycolide. In some embodiments, the medical device may comprise PEG. The abbreviation "PEG" refers to poly (ethylene glycol). In some embodiments, the medical device may comprise PLGA. The abbreviation "PLGA" refers to poly(lactide-co-glycolide) also known as poly(lactic-co-glycolic acid), which are used interchangeably. In some embodiments, the medical device may comprise PLA. The abbreviation "PLA" refers to polylactide. In some embodiments, the medical device may comprise POE. The abbreviation "POE" refers to poly(orthoester).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The section headings are not meant to limit the disclosure and one section heading can be combined with other section headings.

Adhesive Sheet

A new implantable medical device that improves drug efficacy and reduces unwanted migration of the medical device is provided. In various embodiments, new medical devices and methods are provided that effectively prevent, treat or reduce postoperative pain and/or inflammation by providing consistent analgesic and/or anti-inflammatory efficacy at the target tissue site of pain generation. In various embodiments, an adhesive sheet is provided that has a drug depot disposed within one of its regions allowing the surgeon to easily apply pressure to the adhesive sheet causing the drug depot to adhere to the desired target tissue site. In this way, migration of the drug depot away from the target tissue site is inhibited and/or prevented. In various embodiments, the medical device has a removable covering so that the user can "peel and press" the medical device directly at the target tissue site.

In one embodiment, there is a medical device implantable at or near a target tissue site beneath the skin of a patient, the medical device comprising an adhesive sheet having a region configured to receive a drug depot, the drug depot disposed within the region of the adhesive sheet and the drug depot having at least one surface configured to release a therapeutically effective amount of the drug over a period of at least one day, wherein the adhesive sheet limits movement of the medical device at or near the target tissue site.

In some embodiments, the adhesive can be disposed or coated on all or portions of the front and/or back of the sheet or on the drug depot itself. In some embodiments, the adhesive can be disposed or coated on all or portions of the front and/or back of the sheet and/or on the drug depot in a thickness of about 0.1 to about 50 microns. In some embodiments, the drug depot is disposed on or in the front side of the sheet and the adhesive material is disposed on all or a portion of the back of the sheet so that the user presses or applies force to the drug depot containing side of the sheet (e.g., front side) or the drug depots themselves so that the back side of the sheet will adhere to the target tissue and, therefore, keep the drug depot from migrating from the target tissue site.

In some embodiments, the adhesive sheet degrades faster than the drug depot. In some embodiments, the adhesive sheet degrades in the same time or slower than the drug depot. In some embodiments, the adhesive sheet degrades faster than the drug depot (e.g., the adhesive sheet degrades in about six months and the drug depot degrades in about nine months).

The sheet according to the current application is advantageous primarily in that it bonds effectively to tissue, enabling it to be used in a variety of medical applications. In some embodiments, the sheet exhibits good initial adhesion to the tissue to which it is applied (and may thus be described as "self-adhesive"), and furthermore remains well-adhered to the tissue over a longer timescale. Therefore, the drug depot attached to a region of the sheet remains in the proper orientation for release of the therapeutic agent (e.g., as it degrades). Without wishing to be bound by any theory, it is believed that the initial adhesion of the sheet to the tissue is attributable to electronic bonding of the sheet to the tissue, and this is supplemented or replaced by chemical bonding between the tissue-reactive functional groups of the formulation and the tissue. For example, when the adhesive material has amine or thiol groups, there is bonding between amine and/or thiol groups on the tissue surface and the sheet.

The sheet exhibits good initial adhesion to the tissue surface, this being believed to be due to Van der Waals forces and/or hydrogen bonding between the sheet and the tissue surface. In some embodiments, on contact with the tissue surface, the sheet becomes hydrated, thereby causing reaction between the sheet and the underlying tissue surface. Such reactions result in high adhesion between the sheet and the tissue surface. The sheet may absorb physiological fluids (as a consequence of application onto exuding tissue surfaces), and any additional solutions used to hydrate the sheet following application (such fluids can be commonly used solutions used in surgical irrigation), becoming more compliant and adherent to the tissue surfaces, and thereby will provide an adhesive sealant, hemostatic and/or pneumostatic function, if that effect is desired.

The use of the sheet reduces or eliminates the need for additional means of mechanical attachment to the tissue (e.g., sutures or staples). The sheet is applied to the tissue as a preformed article, rather than being prepared by mixing of materials immediately prior to use. The sheet can be any size, shape and configuration and can be in a film, patch, mesh, or the like form. In some embodiments, the adhesive sheet has an overall thickness of from about 0.01 to about 1 mm or from about 0.015 to about 0.05 mm. In some embodiments, the sheet has a tissue contact surface area that accounts for more than 50% of the overall thickness of the sheet.

In some embodiments, it may be necessary or desirable to incorporate into the sheet a scaffold to increase the mechanical strength and/or flexibility of the film for a particular application. Thus, in some embodiments, there is provided an adhesive sheet comprising a homogenous, pre-formed and cross-linked matrix applied to a scaffold material. Suitable materials for the matrix include, for example, one or more poly (alpha-hydroxy acids), poly (lactide-co-glycolide) (PLGA), polylactide (PLA), poly(L-lactide), polyglycolide (PG), polyglycolic acid (PGA), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, tyrosine polycarbonate, chitosan, or combinations thereof.

Suitable scaffolds can comprise biocompatible and biodegradable material. The scaffold conveniently has the form of a sheet of material, the homogeneous, pre-formed and cross-linked matrix being applied to one or both sides of the sheet. In such a case, the product has a multilamellar form. The scaffold may be continuous or may be apertured. In some embodiments, the scaffold is perforated. In some embodiments, the scaffold sheet is formed with an array of perforations and the homogenous film is applied to one or both sides of the scaffold sheet.

In some embodiments, the adhesive sheet comprises an adhesive material that binds tissue. The adhesive material may comprise polymers having hydroxyl, carboxyl, and/or amine groups. In some embodiments, polymers having hydroxyl groups include synthetic polysaccharides, such as for example, cellulose derivatives, such as cellulose ethers (e.g., hydroxypropylcellulose). In some embodiments, the synthetic polymers having a carboxyl group, may comprise poly(acrylic acid), poly(methacrylic acid), poly(vinyl pyrrolidone acrylic acid-N-hydroxysuccinimide), and poly(vinyl pyrrolidone-acrylic acid-acrylic acid-N-hydroxysuccinimide) terpolymer. For example, poly(acrylic acid) with a molecular weight greater than 250,000 or 500,000 may exhibit particularly good adhesive performance. In some embodiments, the adhesive can be a polymer having a molecular weight of about 2,000 to about 5,000, or about 10,000 to about 20,000 or about 30,000 to about 40,000.

In some embodiments, the adhesive can comprise imido ester, p-nitrophenyl carbonate, N-hydroxysuccinimide ester, epoxide, isocyanate, acrylate, vinyl sulfone, orthopyridyldisulfide, maleimide, aldehyde, iodoacetamide or a combination thereof. In some embodiments, the adhesive material can comprise at least one of fibrin, a cyanoacrylate (e.g., N-butyl-2-cyanoacrylate, 2-octyl-cyanoacrylate, etc.), a collagen-based component, a glutaraldehyde glue, a hydrogel, gelatin, an albumin solder, and/or a chitosan adhesives. In some embodiments, the hydrogel comprises acetoacetate esters crosslinked with amino groups or polyethers as mentioned in U.S. Pat. No. 4,708,821. In some embodiments, the adhesive material can comprise poly(hydroxylic) compounds derivatized with acetoacetate groups and/or polyamino compounds derivatized with acetoacetamide groups by themselves or the combination of these compounds crosslinked with an amino-functional crosslinking compounds. In some embodiments, the adhesive comprises one or more poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) poly(lactide-co-glycolide) (PLGA), polylactide (PLA), polyglycolide (PGA), D-lactide, D,L-lactide, L-lactide, D,L-lactide-co-ϵ-caprolactone, D,L-lactide-co-glycolide-co-ϵ-caprolactone, poly(D,L-lactide-co-caprolactone), or poly(L-lactide-co-caprolactone), polyester, or copolymers thereof or combinations thereof.

The adhesive can be a solvent based adhesive, a polymer dispersion adhesive, a contact adhesive, a pressure sensitive adhesive, a reactive adhesive, such as for example multi-part adhesives, one part adhesives, heat curing adhesives, moisture curing adhesives, or a combination thereof or the like. The adhesive can be natural or synthetic or a combination thereof.

Contact adhesives are used in strong bonds with high shear-resistance. Pressure sensitive adhesives form a bond by the application of light pressure to bind the adhesive with the target tissue site and/or drug depot. In some embodiments, to have the device adhere to the target tissue site, pressure is applied in a direction substantially perpendicular to a surgical incision.

Multi-component adhesives harden by mixing two or more components which chemically react. This reaction causes polymers to cross-link into acrylics, urethanes, and/or epoxies. There are several commercial combinations of multi-component adhesives in use in industry. Some of these combinations are: polyester resin-polyurethane resin; polyols-polyurethane resin, acrylic polymers-polyurethane resins or the like. The multi-component resins can be either solvent-based or solvent-less. In some embodiments, the solvents present in the adhesives are a medium for the polyester or the polyurethane resin. Then the solvent is dried during the curing process.

In some embodiments, the adhesive can be a one-part adhesive. One-part adhesives harden via a chemical reaction with an external energy source, such as radiation, heat, and moisture. Ultraviolet (UV) light curing adhesives, also known as light curing materials (LCM), have become popular within the manufacturing sector due to their rapid curing time and strong bond strength. Light curing adhesives are generally acrylic based. The adhesive can be a heat-curing adhesive, where when heat is applied (e.g., body heat), the components react and cross-link. This type of adhesive includes epoxies, urethanes, and/or polyimides. The adhesive can be a moisture curing adhesive that cures when it reacts with moisture present (e.g., bodily fluid) on the substrate surface or in the air. This type of adhesive includes cyanoacrylates or urethanes. The adhesive can have natural components, such as for example, vegetable matter, starch (dextrin), natural resins or from animals e.g. casein or animal glue. The adhesive can have synthetic components based on elastomers, thermoplastics, emulsions, and/or thermosets including epoxy, polyurethane, cyanoacrylate, or acrylic polymers.

Adhesive sheets and adhesives materials suitable for use in the present application are disclosed in published application US20100297218, U.S. Ser. No. 12/602,468, filed Sep. 19, 2007, published application US20090287313, U.S. Ser. No. 12/509,687, filed Jul. 27, 2009, published application US20090044895, U.S. Ser. No. 12/278,252, filed Feb. 2, 2007, published application US 20090018575, U.S. Ser. No. 12/281,289, filed Mar. 1, 2007 and U.S. Pat. Nos. 6,197,296, 7,727,547 and 6,239,190. These entire disclosures are herein incorporated by reference into the present disclosure. A suitable adhesive sheet is available from Tissuemed Limited, UK and can be modified to hold the drug depots.

In some embodiments, the adhesive material comprises less than 50 wt. %, less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. % of the medical device.

The adhesive material, and/or adhesive sheet can be biodegradable and can also contain a therapeutic agent in addition to the therapeutic agent in the drug depot. The therapeutic agent can be in immediate release and sustained release form and disposed in a region or throughout the adhesive sheet.

In some embodiments, the medical device is designed that the majority of the drug depot or surface area of the drug depot contacts the target tissue site and/or bodily fluid to maximize release of the therapeutic agent from the drug depot. In some embodiments, the sheet has a plurality of holes in it placed above, below, front side, back side and/or continuously with the drug depot so that fluid can contact the drug depot and the therapeutic agent can be released from the drug depot.

In some embodiments, the sheet may be prepared by dissolving or dispersing the components of the matrix in a suitable solvent, and casting the resulting solution into a suitable mold or onto a suitable plate. This can be followed by drying to remove solvent and curing to achieve the desired degree of cross-linking, if cross-linking is desired. Curing can be promoted by prolonged application of elevated temperatures (typically several hours at temperatures in excess of 60° C.). In some embodiments, the sheet will have a water content of less than 10% w/w, and more commonly less than 5% w/w.

Three-dimensional articles (e.g., plugs, meshes, patches, etc.) may similarly be prepared by filling of molds with liquid formulations. Sheets comprising a structural scaffold may be prepared by casting the liquid formulation onto the scaffold, by dipping of the scaffold in the liquid formulation or by spraying the formulations onto the scaffold. If the scaffold is required as a backing on one side of the sheet, it may be added during or after the curing process.

Likewise, coatings may be applied to medical devices by casting the formulation over the device, dipping of the devices in liquid formulations or by spraying the devices with the liquid formulation.

In some embodiments, sheets and other formulations may be made up from the following ingredients in the proportions indicated: synthetic polymer(s) with functional groups of from: preferably 20-80% w/w, more preferably 20-70% w/w, 30-60% w/w or 40-60% w/w; additional synthetic polymer(s): preferably 0-30% w/w, more preferably 0-20% w/w or 5-20% w/w; plasticizer(s): preferably 0-30% w/w, more preferably 10-30% w/w or 10-20% w/w; animated and/or thiolated polymer(s): preferably 0-10% w/w, more preferably 2-8% w/w; and non-adhesive film-forming polymer(s): preferably 0-10% w/w, more preferably 0-5% w/w.

The sheet according to the current application is suitable for application to internal surfaces of the body, e.g., it may be applied to internal surfaces such as surfaces of internal organs exposed during surgical procedures, including conventional and minimally invasive surgery. In one embodiment, the sheet comprises a drug depot and comprises an analgesic and/or anti-inflammatory agent that can be used to treat post operative pain.

Drug Depot

The adhesive sheet comprises a region where the drug depot can be placed. In some embodiments, the region is configured to receive the drug depot and comprises one or more channels, holes, grooves, slits, loops, and/or bands and the drug depot can have reciprocating or complementary channels, holes, grooves, slits, loops, and/or bands to fit into the region of the adhesive sheet.

The drug depot releases the therapeutic agent. When referring to therapeutic agent, unless otherwise specified or apparent from context it is understood that the inventor is also referring to pharmaceutically acceptable equivalents or derivatives thereof, such as their pharmaceutically acceptable salts, esters, non-esters, prodrugs or active metabolites. Isomers of all disclosed agents are also encompassed by this disclosure.

Some examples of pharmaceutically acceptable salts include those salt-forming acids and bases that do not substantially increase the toxicity of a compound, such as, salts of alkali metals such as magnesium, potassium and ammonium, salts of mineral acids such as hydriodic, hydrochloric, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Further, when referring to therapeutic agent and other active ingredients, they may not only be in the salt form, but also in the base form (e.g., free base). Pharmaceutically acceptable salts of therapeutic agent include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, or the like.

When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, or the like. Fatty acid salts may also be used, e.g., fatty acid salts having greater than 2 carbons, greater than 8 carbons or greater than 16 carbons, such as butyric, caprioc, caprylic, capric, lauric, mystiric, palmitic, stearic, arachidic or the like.

In some embodiments, the therapeutic agent can be in esterified forms, non-esterified forms or a combination thereof.

The loading of the therapeutic agent in the medical device (e.g., in percent by weight relative to the weight of the basic structure) can vary over a wide range, depending on the specific application, and can be determined specifically for the particular case. In some embodiments, the therapeutic agent is in the medical device (e.g., drug depot) in an amount from about 0.1 wt. % to about 50 wt. %, or about 1 wt. % to about 30 wt. %, or about 2.5 wt. % to about 25 wt. %, or about 5 wt. % to about 25 wt. %, or about 10 wt. % to about 20 wt.

%, or about 5 wt. % to about 15 wt. %, 5 wt. % to about 10 wt. % based on the total weight of the medical device.

In some embodiment there is a higher loading of therapeutic agent, e.g., at least 20 wt. %, at least 30 wt. %, at least 40 wt. %, at least 50 wt. %, at least 60 wt. %, at least 70 wt. %, at least 80 wt. %, or at least 90 wt. %.

In some embodiments, the dosage of therapeutic agent may be from approximately 0.0005 to approximately 500 mg/day. In some embodiments, the amount of therapeutic agent is between 1 mg, 2 mg, 3 mg, 4 mg, 5 mg, 6 mg, 7 mg, 8 mg, 9 mg and 10 mg/day. Additional dosages of therapeutic agent include from approximately 0.0005 to approximately 50 μg/day; approximately 0.0005 to approximately 25 μg/day; approximately 0.0005 to approximately 10 μg/day; approximately 0.0005 to approximately 5 μg/day; approximately 0.0005 to approximately 1 μg/day; approximately 0.0005 to approximately 0.75 μg/day; approximately 0.0005 to approximately 0.5 μg/day; approximately 0.0005 to approximately 0.25 μg/day; approximately 0.0005 to approximately 0.1 μg/day; approximately 0.0005 to approximately 0.075 μg/day; approximately 0.0005 to approximately 0.05 μg/day; approximately 0.001 to approximately 0.025 μg/day; approximately 0.001 to approximately 0.01 μg/day; approximately 0.001 to approximately 0.0075 μg/day; approximately 0.001 to approximately 0.005 μg/day; approximately 0.001 to approximately 0.025 μg/day; and approximately 0.002 μg/day. In another embodiment, the dosage of therapeutic agent is from approximately 0.001 to approximately 15 μg/day. In another embodiment, the dosage of therapeutic agent is from approximately 0.001 to approximately 10 μg/day. In another embodiment, the dosage of therapeutic agent is from approximately 0.001 to approximately 5 μg/day. In another embodiment, the dosage of therapeutic agent is from approximately 0.001 to 2.5 μg/day. In some embodiments, the amount of therapeutic agent is between 200 μg/day and 400 μg/day.

In some embodiments, the therapeutic agent comprises clonidine base, clonidine hydrochloride, or a combination thereof. The medical device may release a dosage of clonidine, which may be from approximately 0.0005 to approximately 960 μg/day. Additional dosages of clonidine include from approximately 0.0005 to approximately 900 ng/day; approximately 0.0005 to approximately 500 μg/day; approximately 0.0005 to approximately 250 μg/day; approximately 0.0005 to approximately 100 μg/day; approximately 0.0005 to approximately 75 μg/day; approximately 0.001 to approximately 70 μg/day; approximately 0.001 to approximately 65 μg/day; approximately 0.001 to approximately 60 μg/day; approximately 0.001 to approximately 55 μg/day; approximately 0.001 to approximately 50 μg/day; approximately 0.001 to approximately 45 μg/day; approximately 0.001 to approximately 40 μg/day; approximately 0.001 to approximately 35 μg/day; approximately 0.0025 to approximately 30 μg/day; approximately 0.0025 to approximately 25 μg/day; approximately 0.0025 to approximately 20 μg/day; approximately 0.0025 to approximately 15 μg/day; approximately 0.0025 to approximately 10 μg/day; approximately 0.0025 to approximately 5 μg/day; and approximately 0.0025 to approximately 2.5 μg/day. In another embodiment, the dosage of clonidine is from approximately 0.005 to approximately 15 μg/day. In another embodiment, the dosage of clonidine is from approximately 0.005 to approximately 10 μg/day. In another embodiment, the dosage of clonidine is from approximately 0.005 to approximately 5 μg/day. In another embodiment, the dosage of clonidine is from approximately 0.005 to 2.5 μg/day. In some embodiments, the amount of clonidine is between 40 and 600 μg/day. In some embodiments, the amount of clonidine is between 200 and 400 μg/day.

The average molecular weight of the polymer of the depot can be from about 1000 to about 10,000,000; or about 1,000 to about 1,000,000; or about 5,000 to about 500,000; or about 10,000 to about 100,000 or about 125,000; or about 20,000 to 50,000 daltons.

In various embodiments, the polymer of the depot or the depot has a molecular weight, as shown by the inherent viscosity (IV), from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

The particle size of the therapeutic agent in the depot (e.g., clonidine) can be from about 1 to about 25 micrometers, or about 5 to 30 or 50 micrometers, however, in various embodiments ranges from about 1 micron to 250 microns may be used.

The therapeutic agent or its pharmaceutically acceptable salt, esters and non-esters thereof may be administered with a muscle relaxant. Exemplary muscle relaxants include by way of example and not limitation, alcuronium chloride, atracurium bescylate, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The medical device (e.g., drug depot) may comprise other therapeutic agents in addition to the therapeutic agent as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as glucocorticoids, antioxidants, such as dithiocarbamate, and other compounds, such as, for example, sulfasalazine.

Examples of therapeutic agents suitable for use also include, but are not limited to an anti-inflammatory agent, an analgesic agent, or an osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin or tolmetin; as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivacaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

The therapeutic agent in the device may include, but is not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenetic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein) or combinations thereof.

In some embodiments, the device comprises osteogenic proteins. Exemplary osteogenic proteins include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-beta. As used herein, the terms "morphogen," "bone morphogen," "BMP," "osteogenic protein" and "osteogenic factor" embrace the class of proteins typified by human osteogenic protein 1 (hOP-1).

Exemplary growth factors include, but are not limited to, members of the transforming growth factor beta family, including bone morphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vgl, Vgr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily.

The therapeutic agent may also be administered with non-active ingredients and they may be in the device with the therapeutic agent. These non-active ingredients may have multi-functional purposes including the carrying, stabilizing, pore forming agents, and/or plasticizers controlling the release of the therapeutic agent(s). Plasticizers include polyhydroxy compounds such as a carbohydrate, a polyhydroxy aldehyde, a polyhydroxy ketone, a glycogen, an aldose, a sugar, a mono- or polysaccharide, an oligosaccharide, a polyhydroxy carboxylic compound, polyhydroxy ester compound, a cyclodextrin, a polyethylene glycol polymer, a glycerol an alginate, a chitosan, a polypropylene glycol polymer, a polyoxyethylene-polyoxypropylene block co-polymer, agar, or hyaluronic acid or polyhydroxy derivative compounds, hydroxypropyl cellulose, tween, sorbitan, sorbitan monolaurate, sorbitan monopalmitate, sorbitan monostearate, sorbitan tristearate, sorbitan monooleate, or a combination thereof.

The sustained release process for drug delivery using the medical device, for example, may be by a solution-diffusion mechanism or it may be governed by an erosion-sustained process. In some embodiments, the medical device (e.g., depot) will be a solid or semi-solid formulation containing a biocompatible material that can be biodegradable. In some embodiments, the medical device (e.g., depot) will be a liquid, suspension, and/or gel formulation containing a biocompatible material that can be biodegradable.

Exemplary excipients that may be formulated with the therapeutic agent in addition to the biodegradable polymer include but are not limited to MgO (e.g., 1 wt. %), 5050 DLG 6E (Surmodics Pharmaceuticals, Birmingham, Ala.), 5050 DLG 1A (Surmodics Pharmaceuticals, Birmingham, Ala.), mPEG, TBO-Ac, mPEG, Span-65, Span-85, pluronic F127, TBO-Ac, sorbitol, cyclodextrin, maltodextrin, pluronic F68, CaCl, mannitol, trehalose, and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 5 wt. % of the formulation. In some embodiments, the excipients comprise from about 0.001 wt. % to about 2 wt. % of the formulation.

In various embodiments, the non-active ingredients will be durable within the tissue site for a period of time equal to or greater than (for biodegradable components) or greater than (for non-biodegradable components) the planned period of drug delivery.

In some embodiments, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s). Non-biodegradable polymers include but are not limited to PVC and polyurethane.

In some embodiments, the drug depot may not be fully biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics, methacrylates, poly (N-isopropylacrylamide), PEO-PPO-PEO (pluronics) or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioerodible, a bioabsorbable, and/or a biodegradable biopolymer that may provide immediate release, or sustained release of the therapeutic agent. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) poly(lactide-co-glycolide) (PLGA), polylactide (PLA), polyglycolide (PGA), D-lactide, D,L-lactide, L-lactide, D,L-lactide-co-$\epsilon$-caprolactone, D,L-lactide-co-glycolide-co-$\epsilon$-caprolactone, poly(D,L-lactide-co-caprolactone), or poly(L-lactide-co-caprolactone), or copolymers thereof or combinations thereof. PEG may be used as a plasticizer for PLGA, but other polymers/excipients may be used to achieve the same effect. PEG imparts malleability to the resulting formulations. In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot.

In various embodiments, the drug depot comprises poly (lactide-co-glycolide) (PLGA), polylactide (PLA), polyglycolide (PGA), D-lactide, D,L-lactide, L-lactide, D,L-lactide-co-$\epsilon$-caprolactone, D,L-lactide-co-glycolide-co-$\epsilon$-caprolactone, poly(lactide-co-glycolide) (PLGA), polylactide (PLA), polyglycolide (PGA), D-lactide, D,L-lactide, L-lactide, D,L-lactide-co-$\epsilon$-caprolactone, D,L-lactide-co-glycolide-co-$\epsilon$-caprolactone, poly(D,L-lactide-co-caprolactone), or poly(L-lactide-co-caprolactone), or copolymers thereof or a combination thereof.

In some embodiments, the drug depot comprises one or more polymers (e.g., PLA, PLGA, etc.) having a MW of from about 15,000 to about 150,000 Da or from about 25,000 to about 100,000 Da.

In some embodiments, the implantable depot compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower initial burst and a regulated duration of delivery.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/ or cohesion modifiers. If the depot is to be placed in the spinal area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet (e.g., ribbon-like) or the like. Flexibility may be a consideration so as to facilitate placement of the drug depot. In various embodiments, the drug depot can be different sizes, for example, the drug depot may be a length of from about 0.5 mm to 5 mm, or 1.0 mm, 1.5 mm, 2.0 mm, 2.5 mm, 3.0 mm, 3.5 mm, 4.0 mm, 4.5 mm and have a diameter of from about 0.01 to about 4 mm, for example, 0.25 mm, 0.5 mm, 0.75 mm, or 1.0 mm, 1.25 mm, 1.5 mm, 1.75 mm, 2.0 mm, 2.5 mm, 3.0 mm, 3.5 mm, or 4.0 mm. In various embodiments, as the diameter decreases, the surface area that comes in contact with the bodily fluid of the depot increases and therefore release of the drug from the depot increases. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles. In various embodiments, the radiographic marker could be embedded in the adhesive sheet polymer, a spherical shape or a ring around the depot.

The depot can be different sizes, shapes and configurations, such as for example, strip, rod, sheet, mesh, or the like. There are several factors that can be taken into consideration in determining the size, shape and configuration of the drug depot. For example, both the size and shape may allow for ease in positioning the drug depot at the target tissue site that is selected as the implantation site. In addition, the shape and size of the system should be selected so as to minimize or prevent the drug depot from moving after implantation or injection. In various embodiments, the drug depot can be shaped like a pellet, a sphere, a cylinder such as a rod, a flat surface such as a disc, film or sheet, strip, rod, mesh, or the like. Flexibility may be a consideration so as to facilitate placement of the drug depot. In various embodiments, the drug depot can be different sizes, for example, the drug depot may be a length of from about 2 to 4 cm and width of from about 1-2 cm and thickness of from about 0.25 to 1 mm, or length of from about 0.5 mm to 5 cm and have a diameter of from about 0.01 to about 2 mm. In various embodiments, the depot is a strip having dimensions of 2.5 cm×1.5 cm×0.5 mm. In various embodiments, the drug depot may have a layer thickness of from about 0.005 to 1.0 mm, such as, for example, from 0.05 to 0.75 mm.

Gel

In various embodiments, the therapeutic agent is administered in a gel. The gel may have a pre-dosed viscosity in the range of about 1 to about 2000 centipoise (cps), 1 to about 200 cps, or 1 to about 100 cps. After the gel is administered to the target site, the viscosity of the gel will increase and the gel will have a modulus of elasticity (Young's modulus) in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, a depot comprises an adherent gel comprising therapeutic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and the gel can be applied to the adhesive sheet and cause it to stick or to adhere to the target tissue.

In various embodiments, a gel is provided that hardens or stiffens after delivery. Typically, hardening gel formulations may have a pre-dosed modulus of elasticity in the range of about $1 \times 10^2$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times -10^2$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes low-molecular weight polymers. In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000 g/mol.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different MWs, a gel with a high molecular weight provides a stronger matrix and the matrix takes more time to degrade. In contrast, a gel with a low molecular weight degrades more quickly and provides a softer matrix. In various embodiments, the polymer of the depot or the depot has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In some embodiments, if the polymer materials have different chemistries (e.g., high MW DLG 5050 and low MW DL), the high MW polymer may degrade faster than the low MW polymer.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly (N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with therapeutic agent and applied to the adhesive sheet. In one embodiment, the microspheres provide for a sustained release of the therapeutic agent. In yet another embodiment, the gel, which is biodegradable, prevents the microspheres from releasing the therapeutic agent; the microspheres thus do not release the therapeutic agent until they have been released from the gel. For example, a gel may be deployed around a target tissue site (e.g., a nerve root). Dispersed within the gel may be a plurality of microspheres that encapsulate the desired therapeutic agent. Certain of these microspheres degrade once released from the gel, thus releasing the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site. The present invention also contemplates the use of adherent gels to so constrain dispersal of the therapeutic agent. These gels may be deployed, for example, at or near the wound, in a disc space, in a spinal canal, or in surrounding tissue.

FIG. 1 illustrates a front view of one embodiment of the implantable medical device having an adhesive sheet 16 that has a region 10 containing a drug depot in the form of a strip 12 that releases the therapeutic agent. The adhesive sheet comprises an adhesive material 16 disposed around the perimeter 14 of the drug depot, but it is on the back of the sheet (not shown). In the embodiment shown, the region 10 of the adhesive sheet is configured to receive a drug depot. The adhesive sheet's region 10 can be one or more channels, holes, grooves, slits, loops, hooks, bands, eyelets, barbs, posts, tabs, and/or clips, or the like configured to receive the drug depot. The drug depot can also have reciprocating one or more channels, holes, grooves, slits, loops, hooks, eyelets, barbs, posts, tabs, and/or clips, or the like. For example, the depot surface can fit into a reciprocating surface of the adhesive sheet such as, for example, by reciprocating one or more channels, holes, grooves, slits, loops, and/or bands of the adhesive sheet. The drug depot can fit into the adhesive sheet, for example, by sliding it into it or applying the depot to the sheet causing it to stay to the sheet.

In some embodiments, the sheet has a plurality of holes in it placed above, below, front side, back side and/or continuously with the drug depot so that fluid can contact the drug depot and the therapeutic agent can be released from the drug depot. For example, a plurality of holes can be placed across the back of the adhesive sheet and when the drug depot is placed in the adhesive sheet, the back holes allow drug to diffuse out of the holes and exert action at or near the target tissue site.

In the embodiment shown, the adhesive sheet 16 is a flexible or elastic band or loop, where the region 10 is extended or pulled around the perimeter of the drug depot. The depot can now be orientated and placed with pressure at or near the target tissue site where the adhesive and the depot contacts the target tissue site and the adhesive material holds the depot in position so the surface of the drug depot containing the therapeutic agent can be released. The adhesive prevents the drug depot from migrating away from the target tissue site as blood flow or fluid flow in the area increase. In addition, when multiple drug depots (e.g., strips) are implanted, they can be evenly distributed around the target tissue site (e.g., surgical site) to optimize clinical efficacy. In the embodiment shown, the surface area of the adhesive can be 10%, 20%, 30%, 40%, 50%, 60%, 70%, 80%, 90%, 95% less than the surface area of the drug depot.

In the embodiment shown, the adhesive material 18 is disposed only on a portion of the back side of the adhesive sheet. The back of the adhesive sheet, in this embodiment, does not contain any adhesive material so that the user can apply pressure to the front side containing the depot without the adhesive coming in contact with the user's hands and/or instruments. In this way, pressure is applied to the front side of the adhesive sheet, which causes the adhesive material on the back of the sheet to stick to the target tissue site and thereby bond the drug depot to the target tissue site. It will be understood that the adhesive material can be applied to all or a portion of one or both sides of the adhesive sheet.

In some embodiments, the adhesive sheet is flexible and/or elastic and the drug depot is a stiff material. In some embodiments, the adhesive of the adhesive sheet is a dry material and the user presses it against a target tissue site (e.g., open surgical wound) for a few seconds to a few minutes, where the fluid from the site will contact the adhesive (which can be dry and then hydrate it) and the adhesive sheet will stick to the site leaving the drug depot exposed to the target tissue site (e.g., open surgical wound).

Although the medical device (e.g., drug depot, adhesive sheet) is shown as a rectangular shape in FIGS. 1-5. It will be understood by one or ordinary skill in the art that the medical device can be any shape (e.g., pellet, oval, strip, rod, sheet, mesh, patch, or the like). It will also be understood by one of ordinary skill in the art that the adhesive sheet of the drug depot may be an extension from the drug depot. It will be understood by those of ordinary skill in the art that the adhesive sheet may be made from the same or different material than the drug depot.

Surgical procedures can be used to attach the medical device at or near the target tissue site. In such applications, the device is positioned in the desired orientation (e.g., against the tissue plane) at or near the target tissue site with the adhesive material touching the target tissue site so that the adhesive binds to the target tissue site and reduces or inhibits migration of the medical device away from the target tissue site.

Figure 2:
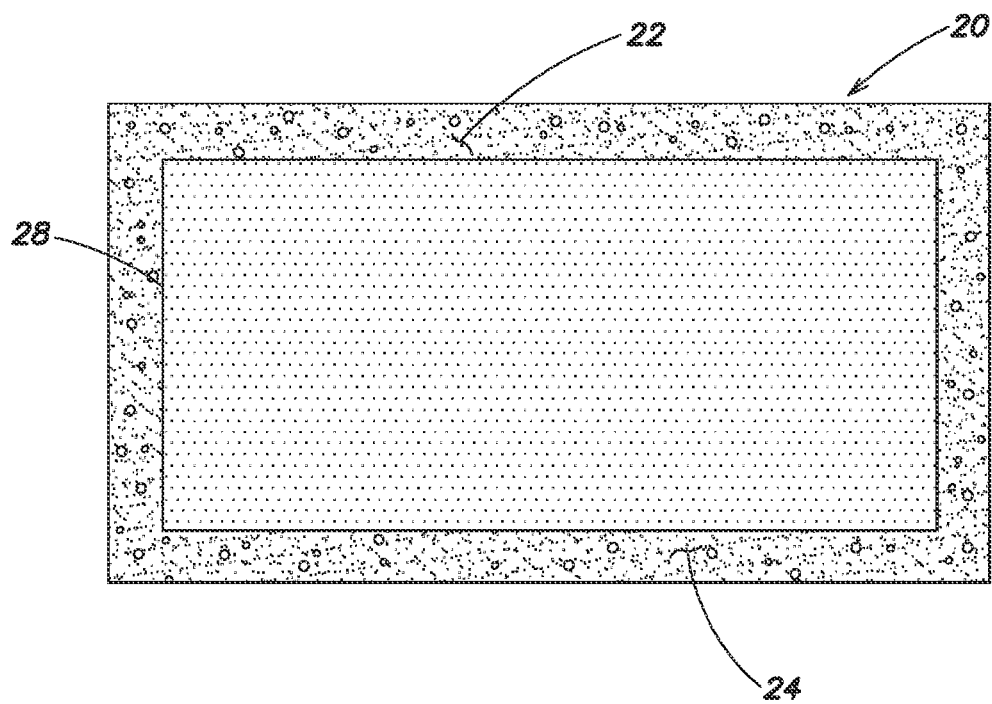
FIG. 2 illustrates a back view of one embodiment of the implantable medical device having an adhesive sheet and a region containing a drug depot in the form of a strip that releases the therapeutic agent. The back of the adhesive sheet has the adhesive material disposed on it so that the device can stick to the target tissue site.

FIG. 2 illustrates a back view of one embodiment of the implantable medical device having an adhesive sheet 20 having an adhesive material 22 and a region 24 containing a drug depot 28 in the form of a strip that releases the therapeutic agent. The adhesive sheet has an adhesive material on the back around the perimeter of it. The user presses on the front side of the medical device, which allows the adhesive to stick to the target tissue site.

In the embodiment shown, the surface area of the adhesive can be 40% less than the surface area of the drug depot. In the embodiment shown, the adhesive material 22 is disposed only on a portion of the back side of the adhesive sheet. The front of the adhesive sheet, in this embodiment, does not contain any adhesive material so that the user can apply pressure to the front side without the adhesive coming in contact with the user's hands and/or instruments. In this way, pressure is applied to the front of the adhesive sheet, which causes the adhesive material on the back of the sheet to stick to the target tissue site and thereby bond the drug depot to the target tissue site. In some embodiments, the drug depot can have a sustained release surface 24 that releases the therapeutic agent in a controlled manner over a extended period of time (e.g., about 3 days, 3 months, 6 months, 9 months or longer). In some embodiments, the adhesive sheet contains immediate release and/or sustained release formulations of the therapeutic agent. In some embodiments, the adhesive sheet contains no therapeutic agent.

In some embodiments, the medical device is designed that the majority of the drug depot or surface area of the drug depot contacts the target tissue site and/or bodily fluid to maximize release of the therapeutic agent from the drug depot. In some embodiments, the sheet has a plurality of holes in it placed above, below or continuously with the drug depot so that fluid can contact the drug depot and the therapeutic agent can be released from the drug depot.

Figure 3:
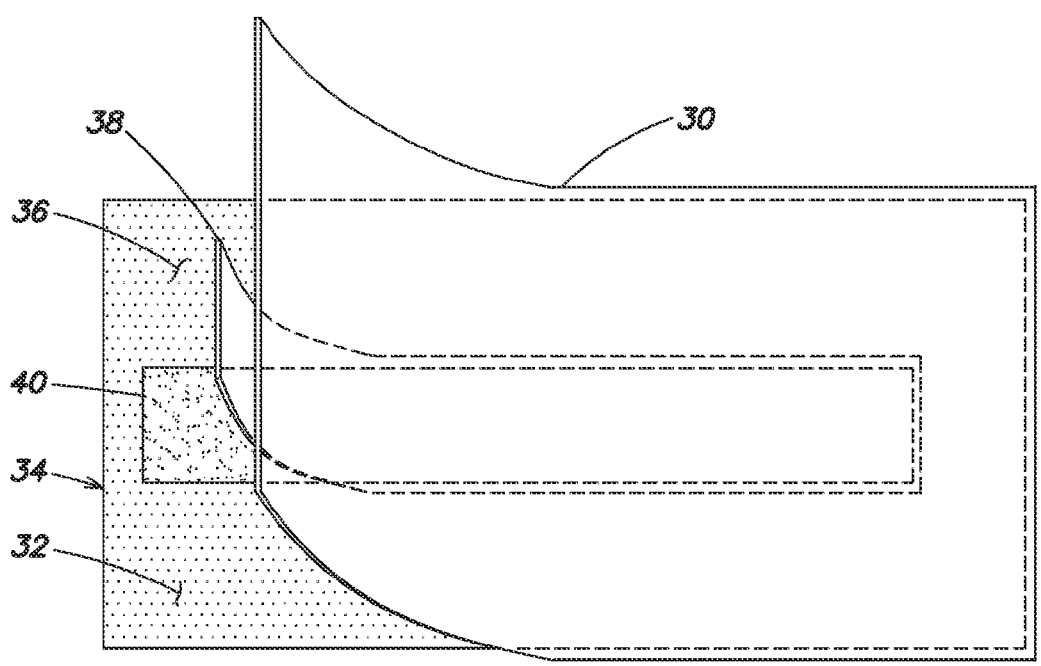
FIG. 3 illustrates a front view of one embodiment of the implantable medical device having an adhesive sheet and a region containing a drug depot in the form of a strip that releases the therapeutic agent. The adhesive sheet and the drug depot optionally both have a removable peel away covering so that the device can be peeled and then stuck to the target tissue site.

FIG. 3 illustrates a front view of one embodiment of the implantable medical device having an adhesive sheet 40 and a region containing a drug depot 34 in the form of a strip that releases the therapeutic agent. The adhesive sheet and the drug depot both have a removable peel away covering 38 and 30, respectively.

In the embodiment shown, the adhesive material 40 is disposed only on a portion of the front side of the adhesive sheet. The back of the adhesive sheet, in this embodiment, does not contain any adhesive material so that the user can apply pressure to the back side of the sheet and/or depot without the adhesive coming in contact with the user's hands and/or instruments. In this way, pressure is applied to the back of the adhesive sheet, which causes the adhesive material on the front of the sheet to stick to the target tissue site and thereby bond the drug depot to the target tissue site. In some embodiments, the drug depot can have an immediate release surface or layer 32 that provides a burst release or bolus dose of the therapeutic agent over a period of 24, or 48 hours and a sustained release surface 36 that releases the therapeutic agent in a controlled manner over a extended period of time (e.g., 3 days or longer). In some embodiments, the adhesive sheet contains immediate release and/or sustained release formulations of the therapeutic agent in addition to the adhesive material. In some embodiments, the adhesive sheet contains no therapeutic agent.

Figure 4:
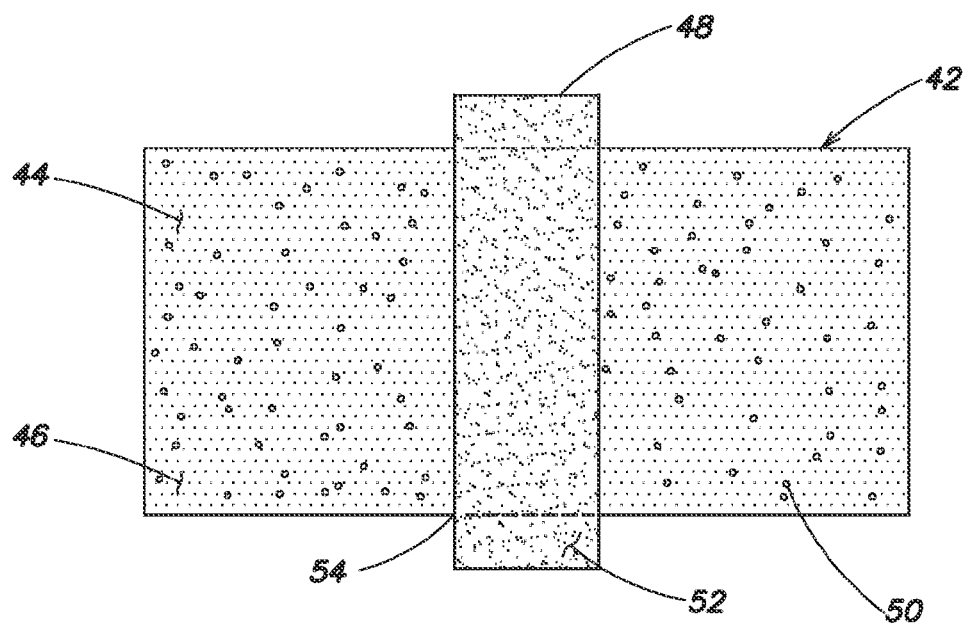
FIG. 4 illustrates a front view of one embodiment of the implantable medical device having an adhesive sheet and a region containing a drug depot that slides into the adhesive sheet. The drug depot is in the form of a strip that releases the therapeutic agent.

FIG. 4 illustrates a front view of one embodiment of the implantable medical device having an adhesive sheet 48 containing an adhesive material 52 disposed on the surface of the adhesive sheet and a region 54 containing a drug depot that slides into the adhesive sheet. The drug depot and/or adhesive sheet, in some embodiments, can have a lubricant on or in its surface to ease sliding movement of the drug depot. The drug depot is shown in the form of a strip 42 that releases the therapeutic agent at or near the target tissue site. In the embodiment shown, the adhesive material 52 is disposed as layers on the front side of the adhesive sheet. The back of the adhesive sheet (not shown), has adhesive material disposed on it so that the medical device can bind two tissue surfaces that come in contact with it. This keeps the drug depot in position. In some embodiments, the drug depot can have an immediate release surface or layer 44 that provides a burst release or bolus dose of the therapeutic agent over a period of 24, or 48 hours and a sustained release surface or layer 46 that releases the therapeutic agent in a controlled manner over a extended period of time (e.g., 3 days or longer). In some embodiments, the drug depot has the therapeutic agent uniformly disposed throughout it as well as pores 50 disposed throughout it that aids in release of the therapeutic agent as fluid comes in contact with the drug depot.

In some embodiments, the region of the adhesive and/or drug depot surface comprises a biocompatible lubricant to reduce the friction when the drug depot as it is contacted with the adhesive sheet. Suitable examples of lubricants include, without limitations, hyaluronic acid, hyaluronan, lubricin, polyethylene glycol, or sorbitol, magnesium stearate, calcium stearate, zinc stearate, stearic acid, hydrogenated vegetable oils, talc, mineral oil or any combinations thereof.

Figure 5:
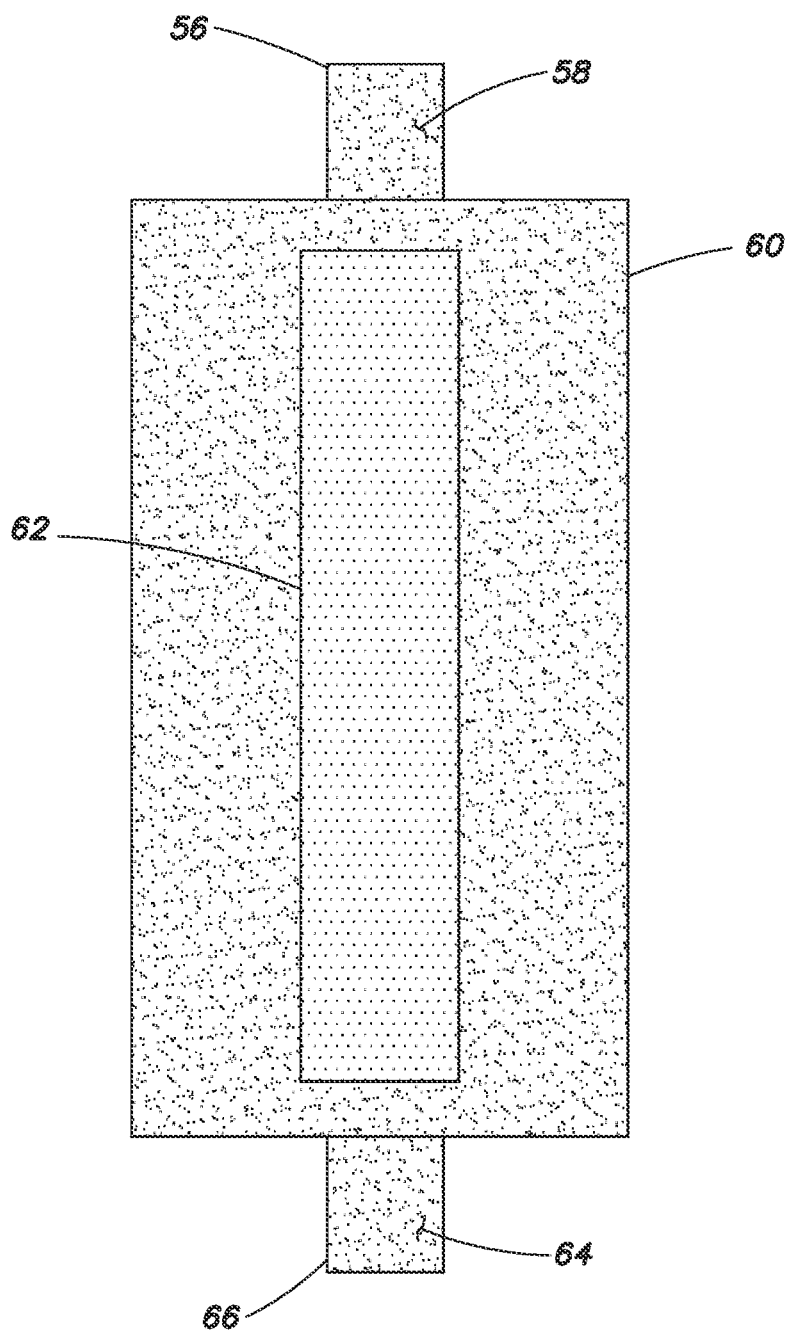
FIG. 5 illustrates a side view of one embodiment of the implantable medical device having an adhesive sheet and a region containing a drug depot that slides into the adhesive sheet. The drug depot is in the form of a strip that releases the therapeutic agent. In this embodiment, the medical device has two tabs that allow the user to peel and press the device at or near the target tissue site.

FIG. 5 illustrates a side view of one embodiment of the implantable medical device having an adhesive sheet 60 and a region containing a drug depot 62 that slides into the adhesive sheet (optionally with the aid of a lubricant on the surface of the adhesive sheet and/or on the drug depot). The drug depot is shown in the form of a strip that releases the therapeutic agent at or near the target tissue site. In the embodiment shown, the adhesive material 60 is disposed as layers on the front side and back side of the adhesive sheet so that the medical device can bind two tissue surfaces that come in contact with them. This keeps the drug depot in position. In some embodiments, the adhesive sheet 60 has lower tab 66 attached to the adhesive sheet containing an adhesive material 64 on one side and upper tab 56 attached to the adhesive sheet containing adhesive material 58 on one side. The other sides of the tabs do not contain adhesive material. These tabs are sized to contact a finger tip. In this way, the user can apply pressure to the back side of the tabs and guide the device in the desired position without the adhesive coming in contact with the user's hands and/or instruments. Thus, the user can peel and press the medical device in position. It will be understood by those of ordinary skill in the art that the depot and/or adhesive can be made from the same or different material.

In some embodiments, the medical device is suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

In some embodiments, there is a method of treating post-operative pain or inflammation in a patient in need of such treatment, the method comprising positioning a medical device at or near a target tissue site beneath the skin of a patient, the medical device comprising an adhesive sheet having an adhesive material disposed on all or a portion of the adhesive sheet, the adhesive sheet having a region containing a drug depot disposed within the region, and the drug depot having a therapeutically effective amount of a drug and at least one surface adapted to release the therapeutically effective amount of the drug over a period of at least one day, and applying pressure to the adhesive sheet and allowing the adhesive material to adhere to the target tissue site so as to limit movement of the medical device at or near the target tissue site.

Method of Making Drug Depot

In various embodiments, the drug depot comprising the therapeutic agent can be made by combining a biocompatible polymer and a therapeutically effective amount of therapeutic agent or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: an therapeutic agent and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: therapeutic agent, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, therapeutic agent may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the drug depot containing the therapeutic agent. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., therapeutic agent), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of therapeutic agent because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as therapeutic agent are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired. Otherwise, the water or moisture exposure will allow the drug to crystallize on the depot and there will be an initial burst effect.

In various embodiments, the drug depot can be prepared by mixing or spraying the drug with the polymer and then molding the depot to the desired shape. In various embodiments, therapeutic agent is used and mixed or sprayed with the PLA, PLGA, or PEG550 polymer, and the resulting depot may be formed by extrusion and dried.

In various embodiments, there is a pharmaceutical formulation comprising: therapeutic agent, wherein the therapeutic agent comprises from about 0.1 wt. % to about 50 wt. % of the formulation, and at least one biodegradable polymer. In some embodiments, the therapeutic agent comprises from about 3 wt. % to about 20 wt. % or 30 wt. %, about 3 wt. % to about 18 wt. %, about 5 wt. % to about 15 wt. % or about 7.5 wt. % to about 12.5 wt. % of the formulation. By way of example, when using a 5%-15% therapeutic agent composition, the mole ratio of therapeutic agent to polymer would be from approximately 16-53 when using an approximately 80 kDalton polymer that has a 267 grams/mole ratio. By way of another example, when using a 5%-15% therapeutic agent base in the composition, the mole ratio of therapeutic agent base to polymer would be from approximately 18-61 with a mole mass of 230 g/mol. In some embodiments, the weight ratio will be in the range of 10-50% assuming a target dose therapeutic dose of ~1 mg/d for 14 days.

In some embodiments, the drug depot comprises at least one biodegradable material in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

In some embodiments, the at least one biodegradable polymer comprises poly(lactic-co-glycolide) (PLGA) or poly (orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In some embodiments, the at least one biodegradable polymer comprises poly(D,L-lactide-co-caprolactone), or poly (L-lactide-co-caprolactone) or copolymers thereof or a combination thereof. The molar ratio of D,L-lactide or L-lactide to caprolactone in the poly(D,L-lactide-co-caprolactone), or poly(L-lactide-co-caprolactone) is 95% D,L-lactide or L-lactide and 5% caprolactone; 90% D,L-lactide or L-lactide and 10% caprolactone; 85% D,L-lactide or L-lactide and 15% caprolactone; 80% D,L-lactide or L-lactide and 20% caprolactone; 75% D,L-lactide or L-lactide and 25% caprolactone; 70% D,L-lactide or L-lactide and 30% caprolactone; 65% D,L-lactide or L-lactide and 35% caprolactone; 60% D,L-lactide or L-lactide and 40% caprolactone; 55% D,L-lactide or L-lactide and 45% caprolactone; 50% D,L-lactide or L-lactide and 50% caprolactone; 45% D,L-lactide or L-lactide and 55% caprolactone; 40% D,L-lactide or L-lactide and 60% caprolactone; 35% D,L-lactide or L-lactide and 65% caprolactone; 30% D,L-lactide or L-lactide and 70% caprolactone; 25% D,L-lactide or L-lactide and 75% caprolactone; 20% D,L-lactide or L-lactide and 80% caprolactone; 15% D,L-lactide or L-lactide and 85% caprolactone; 10% D,L-lactide or L-lactide and 90% caprolactone; or 5% D,L-lactide or L-lactide and 95% caprolactone or copolymers thereof or combinations thereof. In various embodiments, the medical device comprises polymers and copolymers containing various molar ratios of PEG, lactide, glycolide and/or caprolactone.

In various embodiments, the drug particle size (e.g., therapeutic agent) is from about 1 to about 25 micrometers, or about 5 to 50 micrometers, however, in various embodiments it ranges from about 1 micron to 250 microns may be used.

In some embodiments, at least 75% of the particles (e.g., therapeutic agent, drug depot, adhesive) have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles (e.g., therapeutic agent, drug depot, adhesive) have a size from about 20 micrometer to about 180 micrometers. In some embodiments, at least 85% of the particles have a size from about 20 micrometers to about 180 micrometers. In some embodiments, at least 95% of the particles (e.g., therapeutic agent, drug depot, adhesive) have a size from about 20 micrometer to about 180 micrometers. In some embodiments, all of the particles have a size from about 20 micrometer to about 180 micrometers.

In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the therapeutic agent are the only components of the pharmaceutical formulation.

In some embodiments, there is a pharmaceutical formulation comprising: an therapeutic agent, wherein the therapeutic agent is in non-esterified form (does not contain any ester), and comprises from about 0.1 wt. % to about 30 wt. % of the formulation, and at least one biodegradable polymer, wherein the at least one biodegradable polymer comprises poly(lactide-co-glycolide) (or poly(lactic-co-glycolic acid)) or poly (orthoester) or a combination thereof, and said at least one biodegradable polymer comprises at least 70 wt. % of said formulation. This pharmaceutical formulation can be attached to the adhesive sheet.

In some embodiments, there is a pharmaceutical formulation comprising an therapeutic agent, wherein the therapeutic agent is stanozolol and comprises from about 0.1 wt. % to about 30 wt. % of the formulation and a polymer comprises at least 70% of the formulation. In some embodiments, the polymer in this formulation is polyorthoester.

In some embodiments, the formulation comprises a drug depot that comprises a biodegradable polyorthoester. The mechanism of the degradation process of the polyorthoester can be hydrolytical or enzymatical in nature, or both. In various embodiments, the degradation can occur either at the surface of the drug depot (heterogeneous or surface erosion) or uniformly throughout the drug delivery system depot (homogeneous or bulk erosion). Polyorthoester can be obtained from A.P. Pharma, Inc. (Redwood City, Calif.) or through the reaction of a bis(ketene acetal) such as 3,9-diethylidene-2,4, 8,10-tetraoxo spiro [5,5]undecane (DETO SU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, the medical device has a therapeutic agent loading of from about 1 wt % to about 25 wt %, or about 5 wt % to about 10 wt %. In some embodiments, the loading is from about 10 wt % to about 20 wt. %. In some embodiments, the medical device is loaded with between about 5 wt % to about 50 wt % of the therapeutic agent based on the total weight of the medical device. In some embodiments, the medical device is loaded with between about 10 wt % to about 50 wt % of the therapeutic agent based on the total weight of the medical device. In some embodiments, the medical device is loaded with between about 10 wt % to about 30 wt % of the therapeutic agent based on the total weight of the medical device.

In some embodiment there is a higher loading of therapeutic agent, e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (e.g., wound site) such that the target tissue site falls within a region that is either between the formulations when there are two, or within an area whose perimeter is defined by a set of plurality of formulations. The adhesive sheet makes placing a plurality of drug depots easier and maximizes efficacy.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying, jet milling, fitz milling, or cryogrinding. In some embodiments, therapeutic agent is released daily for a period of at least three days. In some embodiments, this release rate continues for, at least seven to twenty-one days. In some embodiments, the therapeutic agent is implanted at multiple sites that triangulate the target site (e.g., wound). In some embodiments, the therapeutically effective dosage amount (e.g., therapeutic agent dose) is released from the drug depot for a period of at least three days to twenty-one days.

In some embodiments the therapeutic agent in the depot is designed for a bolus dose or burst dose within 1, 2, or 3 days after implantation to provide an immediate release of the therapeutic agent for treatment of post-operative pain.

In some embodiments, the medical device is administered parenterally, e.g., by injection. In some embodiments, the injection is intrathecal, which refers to an injection into the spinal canal (intrathecal space surrounding the spinal cord). An injection may also be into a muscle or other tissue. In other embodiments, the medical device is administered by placement into an open patient cavity during surgery.

In some embodiments, the drug depot (i) comprises one or more immediate release layer(s) that is capable of releasing about 5% to about 20% of the therapeutic agent or pharmaceutically acceptable salts thereof relative to a total amount of the therapeutic agent or pharmaceutically acceptable salt thereof loaded in the drug depot over a first period of up to 48 hours and (ii) one or more sustain release layer(s) that is capable of releasing about 21% to about 99% of the therapeutic agent or pharmaceutically acceptable salt thereof relative to a total amount of the therapeutic agent or pharmaceutically acceptable salt thereof loaded in the drug depot over a subsequent period of up to 3 days to 21 days.

In some embodiments, there is a drug depot comprising therapeutic agent and a polymer, wherein the polymer is one more of various embodiments, the drug depot comprises poly (lactide-co-glycolide) (PLGA), polylactide (PLA), polyglycolide (PGA), D-lactide, D,L-lactide, L-lactide, D,L-lactide-co-$\epsilon$-caprolactone, D,L-lactide-co-glycolide-co-$\epsilon$-caprolactone or a combination thereof.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A medical device implantable at or near a target tissue site beneath the skin of a patient, the medical device comprising a sheet having a region including one or more channels, holes, grooves or slits configured to receive a drug depot, the drug depot including loops, hooks, eyelets, barbs, posts, tabs and/or clips corresponding to the one or more channels, holes grooves or slits of the region such that the drug depot lies fixed within the region of the sheet prior to implantation of the medical device, the drug depot having at least one surface configured to release a therapeutically effective amount of the drug over a period of at least one day, wherein the sheet comprises adhesive on at least one surface thereof, the adhesive being spaced apart from the drug depot and configured to limit movement of the drug depot at or near the target tissue site upon contact with tissue and wherein the sheet and the drug depot are biodegradable and the drug depot degrades slower than the sheet.

2. A medical device according to claim 1, wherein the sheet is flexible or elastic and on a pulling force surrounds a perimeter of the drug depot.

3. A medical device according to claim 1, wherein the sheet has a surface area that is less than the surface area of the drug depot.

4. A medical device according to claim 1, wherein the sheet has an adhesive material on at least a portion of both sides of the sheet.

5. A medical device according to claim 1, wherein the region of the sheet and/or the surface of the drug depot has a lubricant.

6. A medical device according to claim 5, wherein the lubricant comprises hyaluronic acid, hyaluronan, lubricin, polyethylene glycol, sorbitol, magnesium stearate, calcium stearate, zinc stearate, stearic acid, hydrogenated vegetable oils, talc, mineral oil or any combinations thereof.

7. A medical device according to claim 1, wherein the sheet has a removable covering to expose the adhesive to the target tissue site.

8. A medical device according to claim 1, wherein the sheet has a surface without adhesive disposed on it and at least one tab having no adhesive on one side, the at least one tab sized to contact a finger tip.

9. A medical device according to claim 1, wherein the drug depot has a first surface and a second surface opposite the first surface and the first surface of the drug depot protrudes through a front side of the sheet and the second surface of the drug depot protrudes through a back side of the sheet so as to allow first and second surfaces to contact the target tissue site.

10. A medical device according to claim 1, wherein the drug depot has a first surface and a second surface opposite the first surface and the first surface of the drug depot protrudes through a front side of the sheet and the second surface of the drug depot aligns with and is covered by a back side of the sheet.

11. A medical device according to claim 1, wherein the medical device is used to treat post-operative pain.

12. A medical device according to claim 1, wherein the drug depot includes an immediate release layer that provides a burst release of the drug within 24 hours and a sustained release layer that releases the drug in a controlled manner over a period of at least 3 days.

13. A medical device implantable at or near a target tissue site beneath the skin of a patient, the medical device comprising a sheet having a region including one or more channels, holes, grooves or slits configured to receive a drug depot, the drug depot including loops, hooks, eyelets, barbs, posts, tabs and/or clips corresponding to the one or more channels, holes grooves or slits of the region such that the drug depot lies fixed within the region of the sheet prior to implantation of the medical device, the drug depot having a therapeutically effective amount of a drug and at least one surface adapted to release the therapeutically effective amount of the drug, wherein the sheet comprises adhesive on at least one surface thereof, the adhesive being spaced apart from the drug depot and configured to limit movement of the medical device at or near the target tissue site upon contact with tissue and the at least one surface of the drug depot releases about 5% to about 45% of an analgesic relative to a total amount of the analgesic loaded in the medical device over a first period of up to 48 hours and about 55% to about 95% of the analgesic relative to a total amount of the analgesic loaded in the medical device over a subsequent period of at least one day and wherein the sheet and the drug depot are biodegradable and the drug depot degrades slower than the sheet.

14. A medical device according to claim 13, wherein the drug depot comprises at least one biodegradable polymer in an amount of at least 70 wt. % or at least 90 wt. %.

15. A medical device according to claim 14, wherein the at least one biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, D, L-lactide-co-glycolide-co-ε-caprolactone, poly(D,L-lactide-co-caprolactone), or poly(L-lactide-co-caprolactone), or copolymers thereof or a combination thereof.

16. A method of treating postoperative pain or inflammation in a patient in need of such treatment, the method comprising positioning a medical device according to claim 1 at or near a target tissue site beneath the skin of a patient, the medical device comprising an adhesive sheet having an adhesive material disposed on all or a portion of the adhesive sheet, the adhesive sheet having a region containing a drug depot disposed within the region, and the drug depot having a therapeutically effective amount of a drug and at least one surface adapted to release the therapeutically effective amount of the drug over a period of at least one day, and applying pressure to the adhesive sheet and allowing the adhesive material to adhere to the target tissue site so as to limit movement of the medical device at or near the target tissue site.

17. A method according to claim 16, wherein (i) the target tissue site comprises a surgical incision; (ii) the region comprises at least one channel configured to receive the drug depot; or (iii) the pressure is applied in a direction substantially perpendicular to a surgical incision.

18. A method according to claim 16, wherein (i) the region comprises one or more holes, grooves, slits, loops, and/or bands configured to receive the drug depot; (ii) the method comprises pulling the adhesive sheet around a perimeter of the drug depot; or (iii) the adhesive sheet has a removable covering and the method comprises removing the removable covering by peeling it in a direction away from the adhesive sheet to expose the adhesive material to the target tissue site.

19. A method according to claim 16, wherein the adhesive sheet has a surface having no adhesive material disposed on it and at least one tab having no adhesive material on one side, the at least one tab sized to contact a finger tip and the method comprises applying pressure to the tab and the surface having no adhesive material to set the adhesive material at the target tissue site.

* * * * *

UNITED STATES PATENT AND TRADEMARK OFFICE
CERTIFICATE OF CORRECTION

| | | |
|---|---|---|
| PATENT NO. | : 9,132,194 B2 | Page 1 of 1 |
| APPLICATION NO. | : 13/180685 | |
| DATED | : September 15, 2015 | |
| INVENTOR(S) | : McKay | |

It is certified that error appears in the above-identified patent and that said Letters Patent is hereby corrected as shown below:

IN THE SPECIFICATION

In Column 8, Line 3, delete "papavereturn," and insert -- papaveretum, --, therefor.

In Column 8, Line 37, delete "TNF-αrelease" and insert -- TNF-α release --, therefor.

In Column 17, Line 43, delete "ng/day;" and insert -- μg/day; --, therefor.

In Column 19, Line 27, delete "papavereturn," and insert -- papaveretum, --, therefor.

Signed and Sealed this
Fifteenth Day of March, 2016

Michelle K. Lee
*Director of the United States Patent and Trademark Office*